United States Patent
Park et al.

[11] Patent Number: 5,880,355
[45] Date of Patent: Mar. 9, 1999

[54] APPARATUS FOR MEASURING CONTAMINATION PARTICLES DURING THE MANUFACTURE OF SEMICONDUCTOR DEVICES

[75] Inventors: Sang-o Park; Jin-sung Kim; Hee-se Kang, all of Suwon; Sang-young Moon, Ansan, all of Rep. of Korea

[73] Assignee: Samsung Electronics Co., Ltd.

[21] Appl. No.: 655,121

[22] Filed: May 28, 1996

[30]     Foreign Application Priority Data

May 29, 1995 [KR]  Rep. of Korea .................. 1995-13695

[51] Int. Cl.⁶ ................................... G01N 15/02
[52] U.S. Cl. ...................... 73/28.01; 73/28.05; 73/865.5; 73/863.22
[58] Field of Search ................................ 73/28.01, 28.04, 73/28.05, 28.06, 865.5, 864.71, 863.22, 865.9

[56]            References Cited
            U.S. PATENT DOCUMENTS 3,888,112   6/1975  De Leeuw et al. ............... 73/28.01 X
4,590,792   5/1986  Chiang ........................... 73/28.06
5,255,555  10/1993  McKeique ........................ 73/28.01

*Primary Examiner*—Michael Brock
*Attorney, Agent, or Firm*—Jones & Volentine, L.L.P.

[57]             ABSTRACT

An apparatus and a method of measuring contamination particles generated during manufacturing of semiconductor devices and an analysis method therefor are described. The apparatus for measuring contamination particles has a regulator for controlling the flow of source gas, a first junction, a first filter, a first air valve, a test component, a second junction, a flow pressure reducer, a third junction, a particle counter, a second pump, a computer system, a third air valve, a flow meter, a second filter, a second air valve, a fourth junction, a third filter, an impactor, and a first pump. It is possible to analyze structures and elements of the contamination particles generated from a gas delivery system (GDS) and from at least one utility component constituting the system. Further, it is possible to set up a reference for controlling the contamination particles generated from the GDS and from at least one of the utility components.

6 Claims, 8 Drawing Sheets

APPARATUS FOR MEASURING CONTAMINATION PARTICLES DURING THE MANUFACTURE OF SEMICONDUCTOR DEVICES

BACKGROUND OF THE INVENTION

The present invention relates to an apparatus and a method of measuring contamination particles generated during manufacturing of semiconductor devices and an analysis method therefor.

More particularly, in one embodiment the present invention relates to an apparatus having the ability to measure individually the contamination particles in a gas utility pipe itself or in each component of a system used in the manufacture of a semiconductor device by a unit process consisting of the components by using a particle shedding system. In a further embodiment, the invention also relates to a method of measuring the contamination particles by using the apparatus of the first embodiment and a method of analyzing the type, the structure and the amounts of contamination particles by sampling contamination particles existing in a gas pipe or in a test sample generated in a pipe of the apparatus which measures contamination particles generated during manufacturing of semiconductor devices.

In view of the advanced manufacturing techniques and high integration of semiconductor devices, contamination particles generated during manufacturing of the semiconductor devices have a direct influence on the yield and the quality of the devices. Accordingly, it is very important to analyze for the presence of contamination particles and to control the level of contamination to the extent possible. However, until this point in time there has been no method for controlling the contamination particles generated from an apparatus during manufacturing of a semiconductor device, i.e., a total gas delivery system (GDS) and in each component constituting the system (for example, a gas filter, a mass flow controller (MFC), and an air valve).

Therefore, if contamination particles are generated from the apparatus for the unit process, it is necessary to find a technique where the contamination particles generated from the GDS are measured and sampled, the structure and elements thereof are analyzed, and the analyzed data are compared with the contamination particles generated from the apparatus for the unit process.

Further, if a contamination particle is generated inside the apparatus or on a wafer, it is necessary to make a reference where contamination particles generated from the GDS are classified. It is also necessary to analyze the structure and make-up (elements) of the contamination particle or particles generated from each gas used for each process of manufacturing semiconductor devices and to thereby systematically classify them.

Many utility components for each use are installed in the GDS which delivers gas for manufacturing semiconductor devices to reaction chambers. The contamination particles generated from the component exert a harmful influence on a following component and cause particle contamination in an actual process.

SUMMARY OF THE INVENTION

It is an object of the present invention to provide an apparatus which measures contamination particles generated during the manufacturing of semiconductor devices.

It is another object of the present invention to provide a method of measuring contamination particles generated during manufacturing of semiconductor devices, using the apparatus which measures contamination particles.

It is still another object of the present invention to provide a method of analyzing contamination particles sampled by the apparatus which measures contamination particles.

To accomplish the above object of the present invention, there is provided an apparatus which measures contamination particles generated during manufacturing of semiconductor devices comprising a regulator for controlling the flow of a source gas which is supplied to the semiconductor device, a first junction connected to the regulator, a first filter connected to the first junction, a first air valve for controlling flow of the gas and connected to the first filter, a test component connected to the first air valve, a second junction connected to the test component, a flow pressure reducer connected to the second junction, a third junction connected to the flow pressure reducer, a particle counter connected to the third junction, a second pump and a computer system connected to the particle counter, a third air valve connected to the first junction, a flow meter for measuring flow of the gas and connected to the third air valve, a second filter connected to the flow meter and the third junction, a second air valve for controlling flow of the gas and connected to the second junction, a fourth junction connected to the second air valve, a third filter connected to the fourth junction, an impactor connected to the fourth junction, and a first pump connected to the impactor.

As shown in FIG. 2, the impactor comprises one variable orifice 44, two stages being a first stage 42a and a second stage 42b, and two nozzles being a first nozzle 40a and a second nozzle 40b. The variable orifice which controls the flow of the gas moving out of the impactor can be selected from one of six kinds, which vary from one another by their diameter size, to thereby variably control the amount of flowing gas by selecting an orifice having a particular diameter size. Accordingly, the variable orifice can be varied to select one of the six different kinds of orifices by exchanging one of the orifices having one of the diameter sizes with a kind having a different diameter size, if needed. Also, each of the two nozzles of the apparatus may be varied by selecting for each a nozzle having a particular diameter size from among the six different types whose diameter sizes are different.

Since the diameters of orifice and of the pair of nozzles can be varied, the orifice and nozzles can be used selectively according to the types of samples. The orifice and nozzles are selected as follows. For a particular sized diameter orifice which may be selected, a pairs of nozzles (a first nozzle having a certain size diameter and a second nozzle having a certain size diameter), in turn, may be selected and utilized. Thus, for each other five sized diameter orifices, a plurality of nozzle sizes for each of the pair of nozzles, in turn, may also be selected and utilized. Accordingly, such permits a great deal of adaptation of the impactor to a wide variety of sample types.

The impactor having the variable orifice sizes and the first and second nozzles, the size of which also may be varied, may be utilized for sampling contamination particles generated during manufacturing of semiconductor devices. The third filter, which is attached to the fourth junction leading to the impactor as shown in FIG. 1, controls the amount of flowing gas coming into the impactor. The third filter also has a means to filter external air if the amount of inflow gas is insufficient such that the impactor needs to supplement (replenish) the inflow gas with air taken from the exterior environment.

The flow pressure reducer serves to lower the pressure of the gas supplied by the gas supplier from the second junction. Accordingly, if the amount of gas coming from the second junction is too much, a portion of the gas may be pumped out by the flow gas reducer to lower the pressure of the gas.

To accomplish another object of the present invention, there is provided a method of measuring contamination particles generated during manufacturing of semiconductor devices having a GDS and a plurality of utility components, comprising the steps of: measuring particles generated from the GDS; and measuring particles generated from at least one of the said plurality of utility components. The apparatus provides a means for measuring the density levels of particles generated from the GDS and the said at least one utility component utilizing either of three methods, alone or in combination, which three methods are a static test method, a dynamic test method and an impact test method.

The static test method is a method of measuring particles shed by supplying the uniform flow of gas to test component 16 as shown in FIG. 1. This is a method for estimating the generation degree of contamination particles under actual use.

The dynamic test method is a method of measuring particles shed by impact according to a momentary change of pressure generated by opening and closing air valve 14a which is installed in front of test component 16 as shown in FIG. 1.

The impact test method is a method of measuring particles generated by physical impact outside of test component 16 while supplying a uniform flow of gas to test component 16 as shown in FIG. 1.

To accomplish still another object of the present invention, there is provided a method of analyzing contamination particles generated during manufacturing of semiconductor devices comprising the steps of: sampling the contamination particles; preparing an analysis sample using the sampled particles; and analyzing the analysis sample.

In the step of sampling the particles by an impact method, the orifice and the first and second nozzles are selected and installed in an impactor. Then, gas is supplied to the impactor. By varying the velocity of the gas, the size of the impact orifice and the diameter of each of the pair of impactor nozzles, the quantity of the flow of gas along with the size of the contamination particles included in the gas may be varied to permit the contamination particles in the gas to be individually or collectively sampled in the impactor stages according to the size of the particles.

In the step of preparing an analysis sample, the impactor is disassembled and cleaned with ultrasonic waves. Then, the impactor is dried with nitrogen ($N_2$). Next, a bare wafer cut to 1.0 cm×0.8 cm in area is cleaned with the ultrasonic waves and dried with $N_2$.

In order to analyze the sample, the form of the sampled particle is analyzed by using an electron probe microanalyzer (EPMA) and the size is measured by using a scanning electron microscope (SEM).

According to the present invention, it is possible to measure the structure and the elements of contamination particles generated from utility components, which are organically connected to each other according to each use, during inflow of gas. Furthermore, the contamination particles can be measured by an adopted process or time, so that this can be used as a reference for controlling contamination particles generated from the GDS.

BRIEF DESCRIPTION OF THE DRAWINGS

The above objects and advantages of the present invention will become more apparent by describing in detail a preferred embodiment thereof with reference to the attached drawings in which.

DETAILED DESCRIPTION OF THE INVENTION

Figure 1:
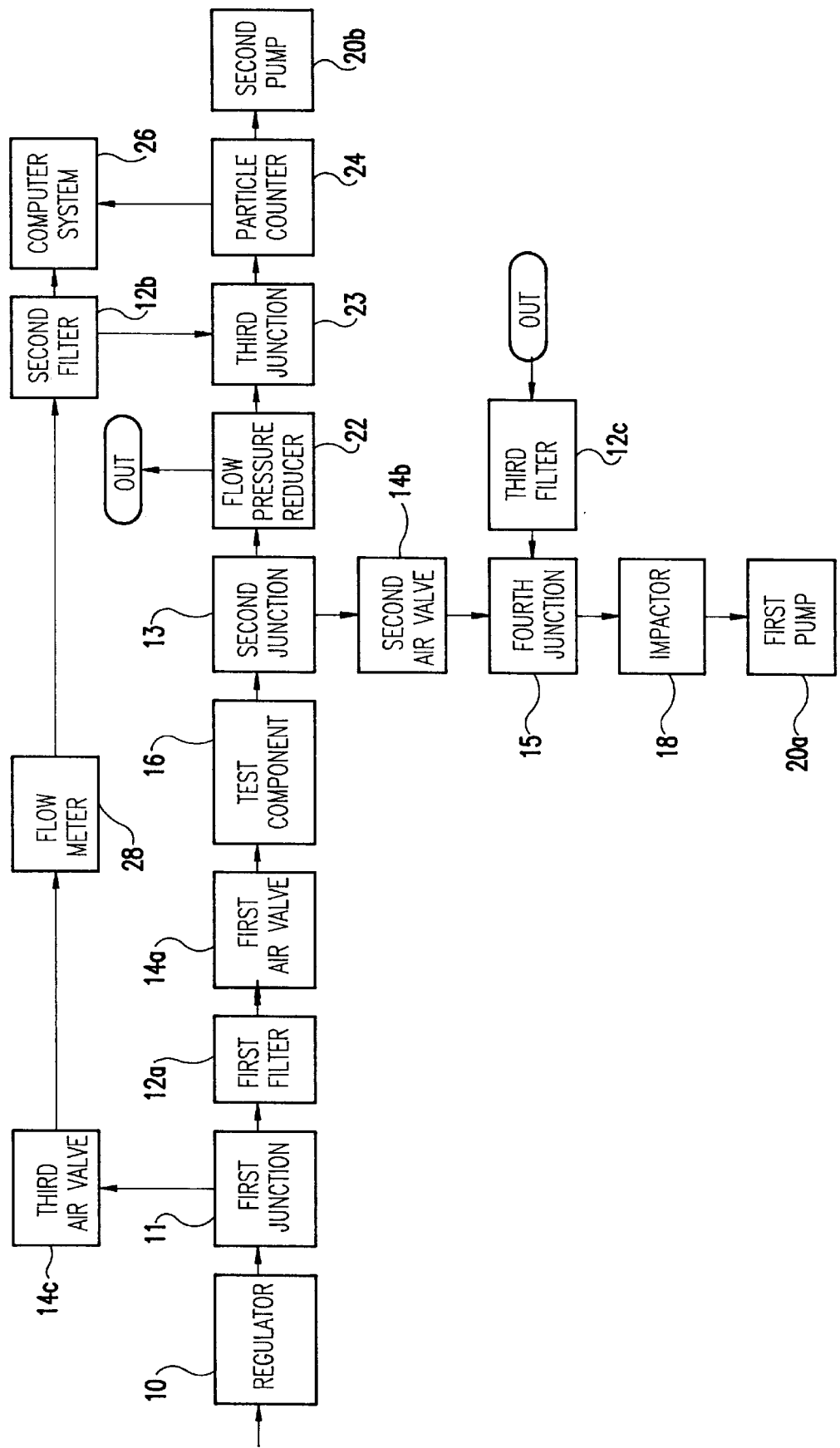
FIG. 1 is a schematic diagram showing an apparatus that measures contamination particles generated during manufacturing of semiconductor devices according to the present invention.

FIG. 1 is a schematic diagram showing an apparatus measuring contamination particles generated during manufacturing of semiconductor devices according to the present invention. The inner structure of the apparatus includes a particle counter 24, a computer system 26, a flow pressure reducer 22 of a particle shedding system for measuring particle contaminations, and an impactor 18 for sampling particle contaminations.

More concretely, the contamination particle measuring apparatus includes a regulator 10 for controlling the flow of source gas which is supplied to the semiconductor devices, a first junction 11 connected to regulator 10, a first filter 12a connected to first junction 11, a first air valve 14a for opening and closing the gas and connected to first filter 12a, a test component 16 connected to the first air valve 14a, a second junction 13 connected to test component 16, a flow pressure reducer 22 connected to second junction 13, a third junction 23 connected to flow pressure reducer 22, a particle counter 24 connected to third junction 23, a second pump 20b and a computer system 26 connected to particle counter 24, a third air valve 14c connected to first junction 11, a flow meter 28 for measuring flow of the gas and connected to third air valve 14c, a second filter 12b connected to flow meter 28 and third junction 23, a second air valve 14b for opening and closing the gas and connected to second junction 13, a fourth junction 15 connected to second air valve 14b, a third filter 12c connected to fourth junction 15, an impactor 18 connected to fourth junction 15, and a first pump 20a connected to impactor 18.

The apparatus for measuring contamination particles operates as follows:

First, particle counter 24 and computer system are turned on. Further, in order to control gas flow suitably and adjust an indication of particle counter 24 to zero, first and second air valves 14a and 14b are closed but third air valve 14c is opened. Then, the flow of gas is controlled by using regulator 10 until the reading on particle counter 24 indicates zero.

Second, when the measured value of particle counter 24 is zero, test component 16 is installed. Then, first and second air valves 14a and 14b are opened and third air valve 14c is closed. The particles are shed and measured by the methods of the static test, the dynamic test and the impact test. At the same time, the shed particles are sampled by impactor 18. The flow of gas which passes through impactor 18 is controlled by orifice 44 of the impactor shown in FIG. 2 and third filter 12c shown in FIG. 1, and the flow of gas which heads towards particle counter 24 is controlled by flow pressure reducer 22.

Third, the structure and the elements of the particle sampled by impactor 18 are analyzed and further compared to a particle on a wafer. Here, for analyzing the structure of the particle SEM is used, and for analyzing the elements, Auger electron spectroscopy (AES) and an EPMA are used.

Figure 2:
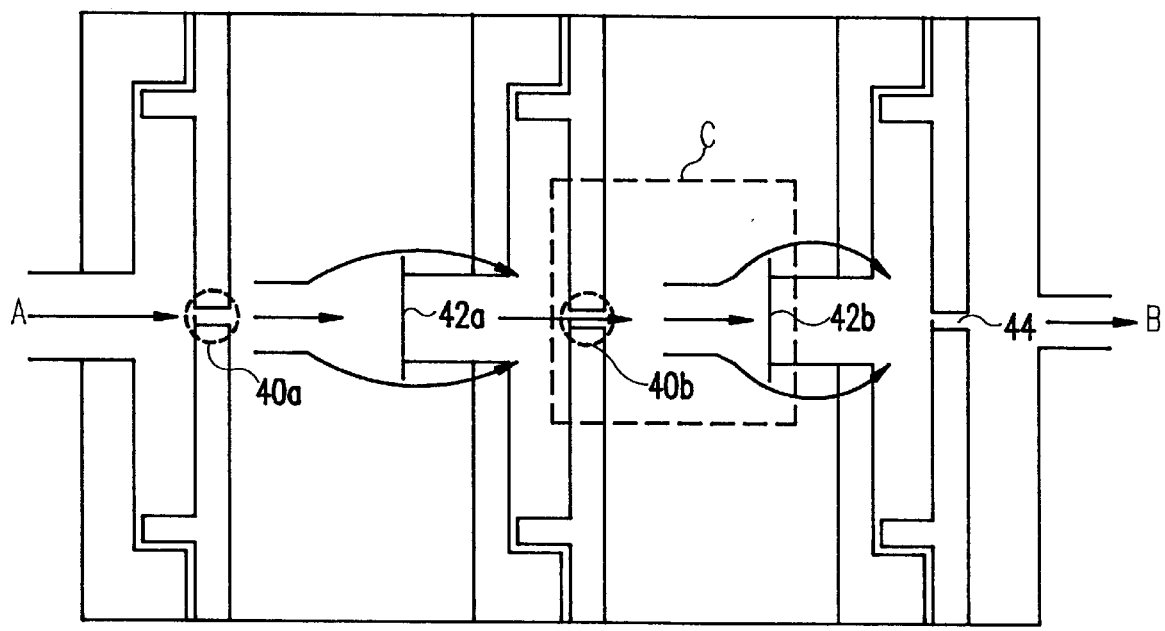
FIG. 2 is a view of the structure of an impactor shown in FIG. 1.

Referring to FIGS. 2 and 3, it will be described in detail how to sample contamination particles by impactor 18.

FIG. 2 is a view of a structure of impactor 18 shown in FIG. 1. The impactor includes an inlet A connected to second air valve 14b shown in FIG. 1 via the fourth junction 15; a pair of nozzles being a first nozzle 40a and a second nozzle 40b, wherein the width size of each of said nozzles may be varied to limit the sort of particles in the gas depending on the diameter of contamination particle(s) which are included in the gas sample; stages 42a and 42b, with one or more having a wafer thereon; and an orifice 44 for controlling the flow of the gas deflating to an outlet B. The outlet B is maintained in a state of vacuum by first pump 20a as shown in FIG. 1. Accordingly, due to the vacuum at outlet B. when the widths of each of nozzles 40a and 40b are wider, gas having larger contamination particles can be flowed into the impactor.

Figure 3A:
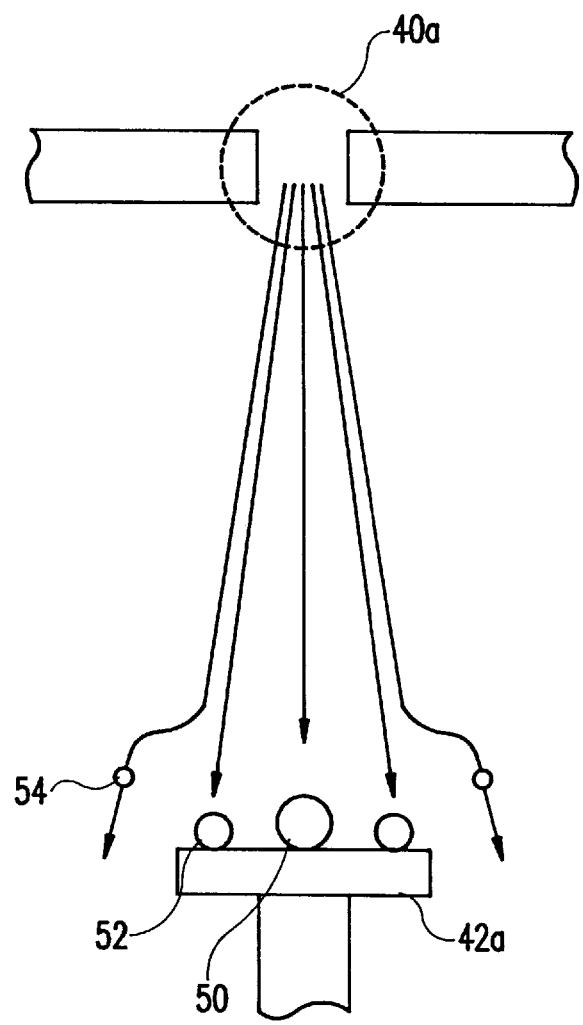
FIGS. 3A and 3B are views illustrating the principle of sampling particles by the impactor shown in FIG. 2.
Figure 3B:
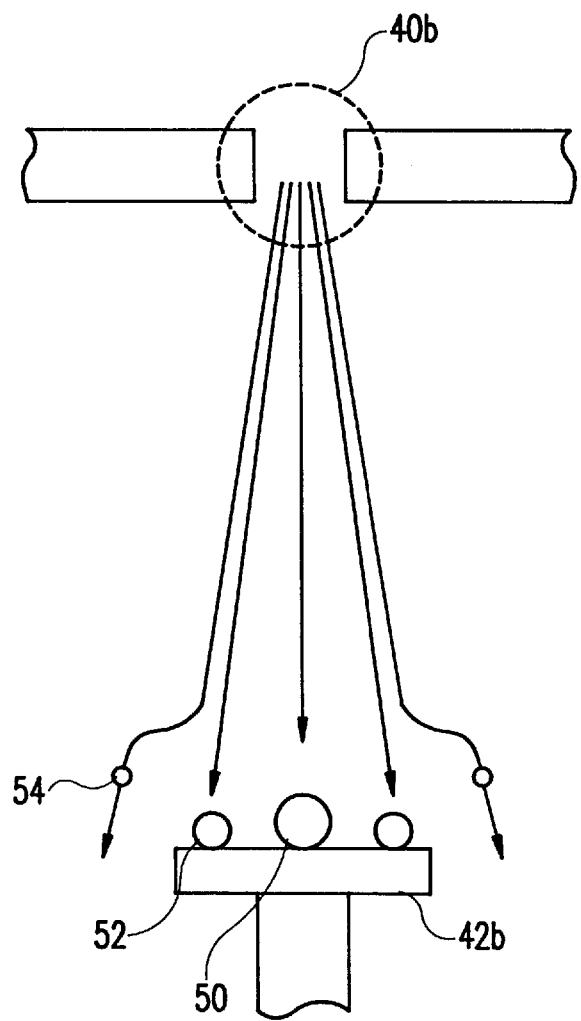

FIGS. 3A and 3B are views illustrating the principle of sampling particles by the impactor as shown in FIG. 2 and each shows an enlarged view of an area of the type marked as area "C" in the FIG. 2 impactor illustration.

More concretely, particles 50 and 52 having a diameter equal to or larger than 0.1 $\mu$m of particles passing through either the impactor nozzle 40a or the impactor nozzle 40b, respectively, as shown in FIG. 2 are sampled by impacting on either a stage 42a or a stage 42b, as the case may be, and particles 54 smaller than 0.1 $\mu$m passing through the impactor together with the gas flow without impacting on either the stage 42a or the stage 42b.

The size of the particle sampled by the stage 42 is expressed by the following formula:

$$d50\ (Cc)^{1/2} = \left( \frac{9\eta D_j (Stk50)}{P_\rho v} \right)^{1/2}$$

where d50 represents the diameter of a particle having possibility of sampling yield of 50%, Cc represents a Cunningham correction factor, $D_j$ represents the diameter of impactor jet, u represents the gas velocity, P$\rho$ represents the particle density (psl:1.05 g/cm$^3$), $\eta$ represents the viscosity of the gas (in case of air), and Stk50 represents stokes number in sampling yield of 50%.

Referring to the formula, the size of the sampled particle is related to the size of the diameter of the nozzle 40a or the nozzle 40b and the flow of the gas and particles through the orifice. Namely, when the flow amount of gas through the orifice is uniform and a constant, as the diameter of the nozzle 40a or 40b becomes smaller, the flow velocity increases, so that smaller particles than particles sampled before the diameter of the nozzle was diminished are sampled by impacting on either stage 42a or 42b. By contrast, under the same conditions if the diameter of the nozzle 40a or 40b becomes larger, the flow velocity decreases, so that larger particles than particles sampled before the diameter of the nozzle was enlarged are sampled by the stage 42a or 42b.

Figure 4:
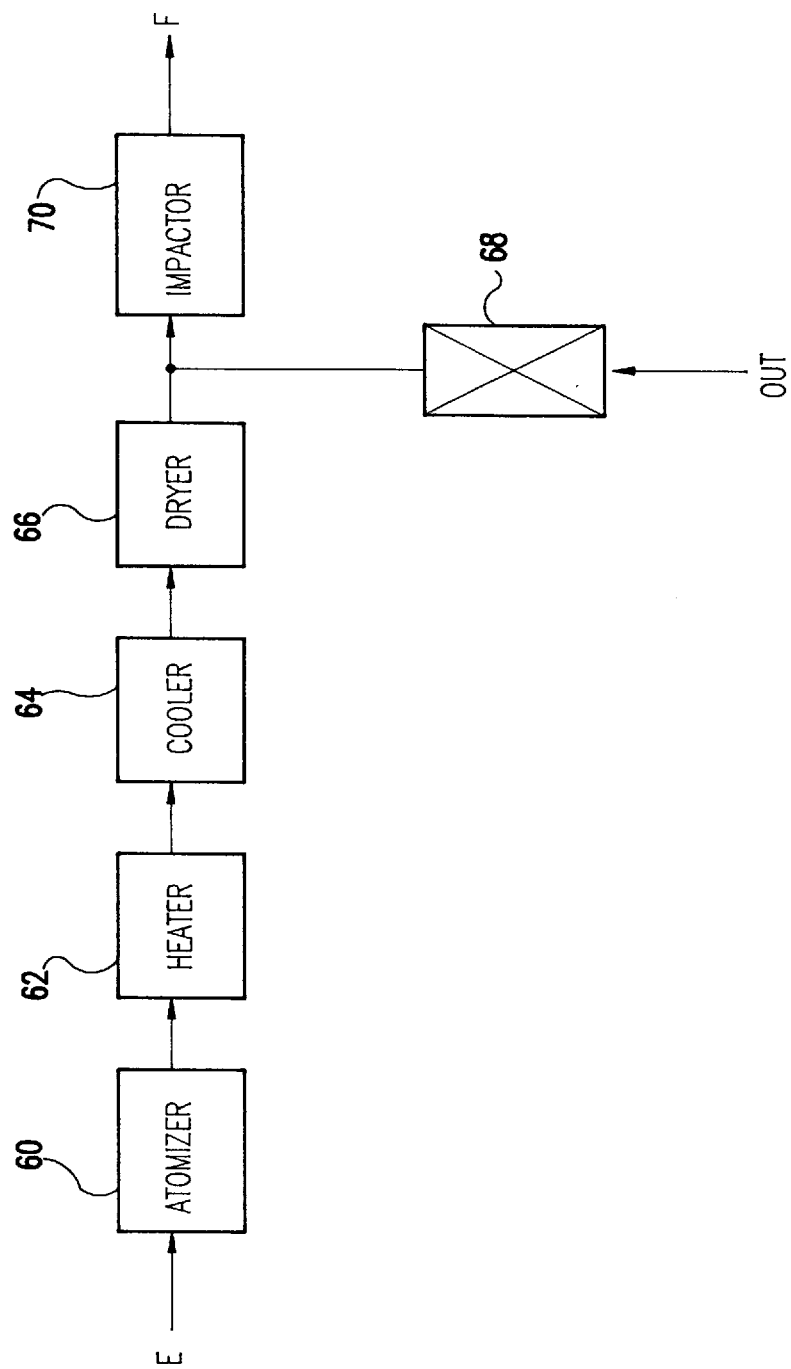
FIG. 4 is a block diagram for estimating a sampling efficiency of contamination particles using an impactor used in the present invention.

FIG. 4 is a block diagram for estimating a sampling efficiency of contamination particles using the impactor used in the present invention. More concretely, E denotes an inlet in which dried N$_2$ flows in. Reference numeral 60 denotes an atomizer, which is an apparatus jetting DI including high-density poly styrene latex (PSL). Reference numeral 62 denotes a heater, in which water and PSL are separated by heating at approximately 150° C. Reference numeral 64 denotes a cooler, which condenses the water separated by heater 62. Reference numeral 66 denotes a diffusion dryer, which absorbs the water remaining in the PSL by using SiO$_2$. Reference numeral 68 is a dilution filter, which properly controls the flow amount flowing into an impactor 70. Reference character F denotes an outlet for the flow-in gas, which is in a state close to vacuum.

For analysis of the particle sampled by impactor 70, impactor 70 is first disassembled and cleaned with ultrasonic waves, and dried with N$_2$. Next, a bare wafer is cut into pieces having the area of 1.0 cm×0.8 cm, and cleaned with ultra sound, and dried with N$_2$. In this manner, the sample analysis preparation is completed.

Accordingly, analysis of the sample is executed as follows.

First, an orifice of a selected size diameter and a pair of nozzles (each being of a selected size diameter) are installed in the impactor, and then contamination particles included in the gas entering the impactor are sampled. One or both of the pair of nozzles can be exchanged for a different size diameter nozzle to vary to correspond to the size needed for the size(s) of contamination particle(s) to be sampled.

Second, the form of the sampled particle is analyzed by using EPMA and the size is determined by using a SEM.

Figure 5A:
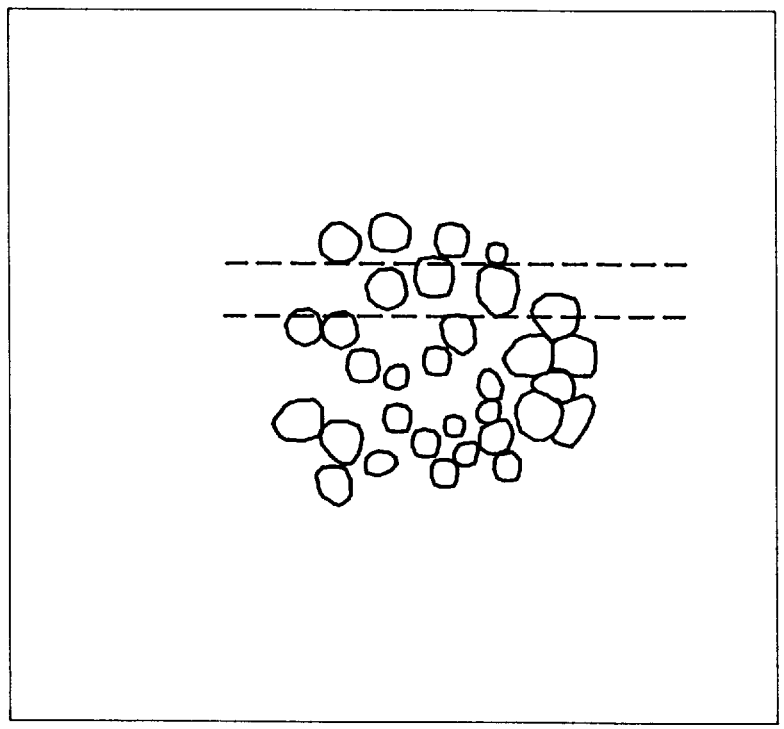
FIGS. 5A and 5B are schematic representations of SEM photographs illustrating examples of contamination particles sampled using the impactor shown in FIG. 2.
Figure 5B:
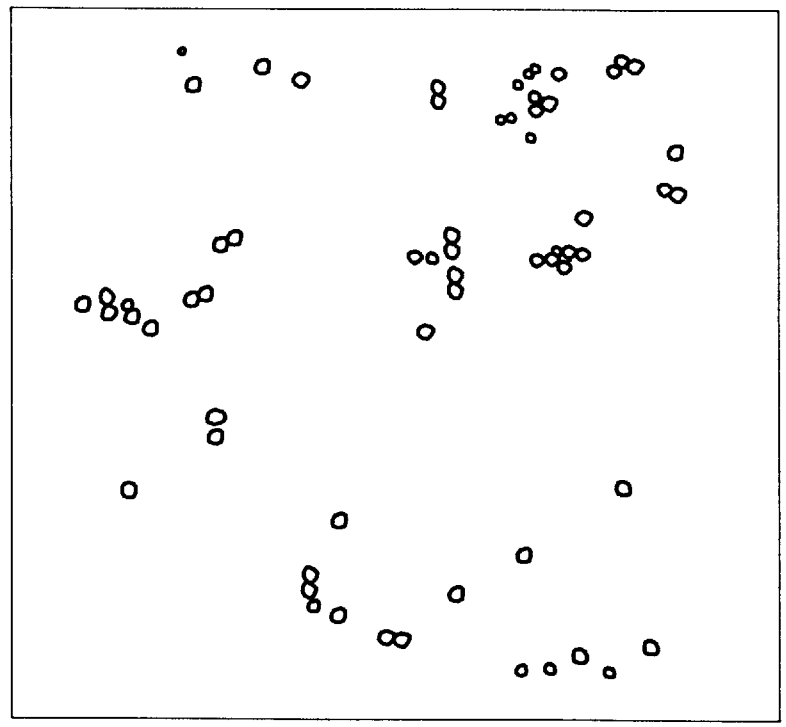

FIGS. 5A and 5B are schematic represntations of SEM photographs illustrating an example of sampling contamination particles by using the impactor shown in FIG. 2.

FIG. 5A is a schematic represntations of a SEM photograph of the contamination particles sampled on one of the stages 42a and 42b shown in FIG. 2, which shows the structure of the impactor, and shows a case in which many small particles, approximately 0.136 $\mu$m, are sampled, with circular form of approximately 0.1 mm in diameter.

FIG. 5B is a schematic represntations of a SEM photograph of the contamination particles sampled on one of the stages 42a and 42b shown in FIG. 2, and further shows a case in which many uniform particles of 1.07 $\mu$m are sampled within a diameter of approximately 1 mm.

Figure 6A:
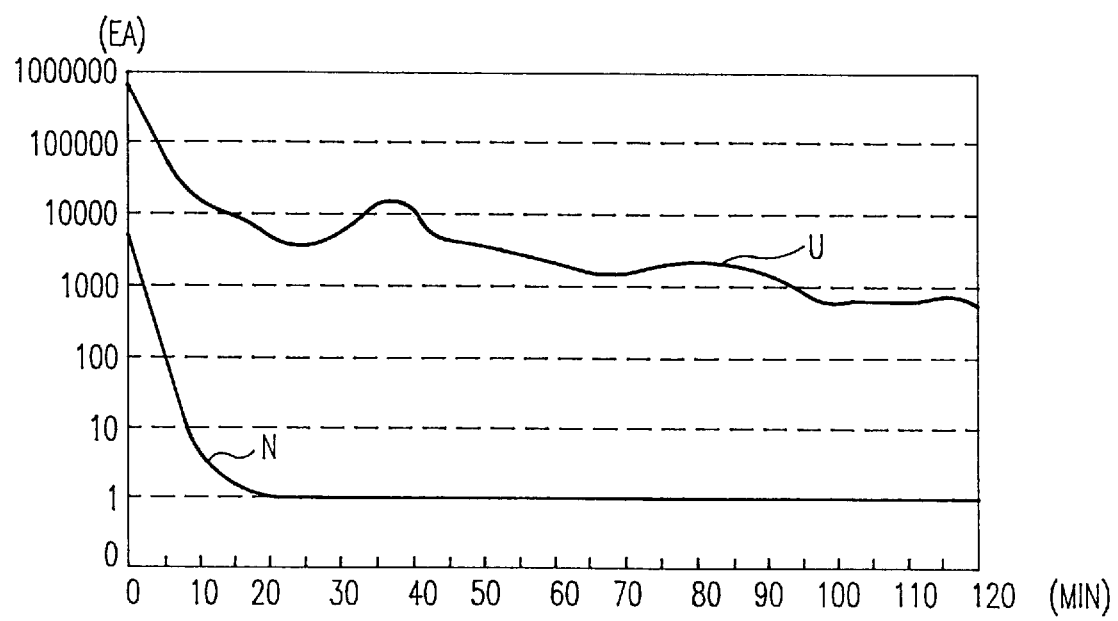
FIGS. 6A through 6C are graphs illustrating the measuring result of particles sampled per minute by the contamination particles measuring apparatus according to the present invention.
Figure 6B:
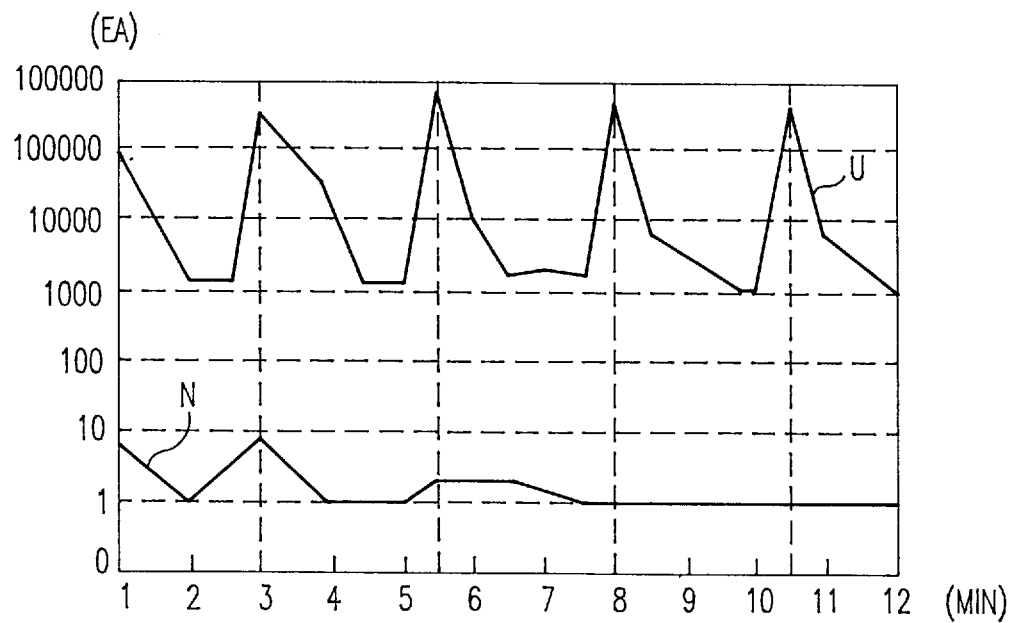
Figure 6C:
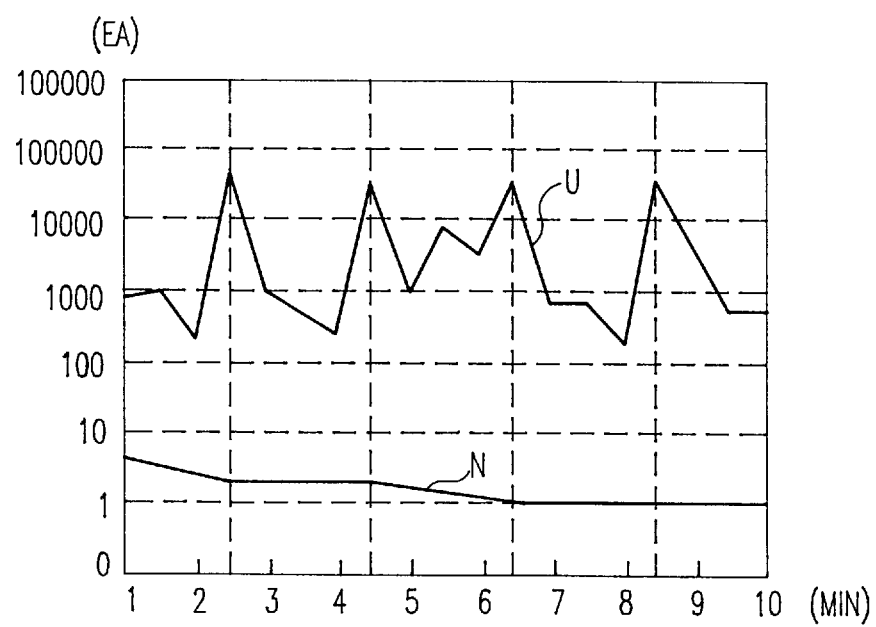

FIGS. 6A through 6C are graphs, each of which illustrates results of measuring particles in a sample by utilizing both a connectional contamination particles measuring apparatus and the contamination particles measuring apparatus according to the present invention. In each of FIGS. 6A–6C, the U denotes results using a conventional mass flow controller (MFC), and N represents results utilizing an apparatus according to the present invention.

FIG. 6A shows the results of measuring particles according to a static test method in which silane SiH$_4$ is used as the gas for the mass flow controller and as the gas for the present apparatus. FIG. 6B shows the result of measuring particles according to a dynamic test method in which SiH$_4$ is used as the gas for the mass flow controller and as the gas for the present apparatus. FIG. 6C shows the result of measuring particles according to an impact test in which SiH$_4$ is used as the gas of the mass flow controller and as the gas for the present apparatus.

According to the present invention, it is possible to find structure and elements of the contamination particle generated from the gas delivery system (GDS) itself and from one or more of the utility components constituting the GDS. Therefore, the contamination particle(s) generated from the GDS and from at least one of the utility components thereof is/are measured for a unit of time by using the GDS and at least one of the utility components and by a process using the system so that it is possible to determine how many contamination particles are generated. The data can be used as the reference for controlling the contamination particles generated from the GDS at a particular point in time and for a particular process being used. Accordingly, it is possible to obtain samples of the contamination particles which are generated from the system and at least one of the utility components constituting the system according to the various sizes of the particles, whereby the structure and elements thereof may be analyzed.

The present invention is not limited to the above embodiments or to the examples illustrated by the described drawings, and many other variations for the present invention can be available to those skilled in this art without departing from the scope of the present invention.

What is claimed is:

1. An apparatus for measuring contamination particles generated during manufacturing of semiconductor devices comprising:

a regulator for controlling the flow of a source gas which is supplied to the semiconductor device;

a first junction connected to said regulator;

a first filter connected to said first junction;

a first air valve for controlling flow of the gas and connected to said first filter;

a test component connected to said first air valve;

a second junction connected to said test component;

a flow pressure reducer connected to said second junction;

a third junction connected to said flow pressure reducer;

a particle counter connected to said third junction;

a second pump and a computer system connected to said particle counter;

a third air valve connected to said first junction;

a flow meter for measuring flow of the gas and connected to said third air valve;

a second filter connected to said flow meter and said third junction;

a second air valve for controlling flow of the gas and connected to said second junction;

a fourth junction connected to said second air valve;

a third filter connected to said fourth junction;

an impactor connected to said fourth junction; and a first pump connected to said impactor, whereby said apparatus provides means for obtaining at least three different types of particle level measurements, either alone or in combination.

2. An apparatus for measuring contamination particles generated during the manufacture of semiconductor devices according to claim 1, wherein said impactor comprises:

an orifice of first size controlling the flow of gas from an inlet through an outlet;

a first nozzle having a first diameter and a second nozzle having a second diameter;

a first stage placed between the first and second nozzle, and a second stage placed between the second nozzle and the orifice.

3. An apparatus for measuring contamination particles generated during the manufacture of semiconductor devices according to claim 2, wherein the first stage and the second stage each comprise a bare wafer.

4. An apparatus for measuring contamination particles generated during the manufacture of semiconductor devices according to claim 2, wherein the first diameter is different from the second diameter.

5. An apparatus for measuring contamination particles generated during the manufacture of semiconductor devices according to claim 2, wherein the first nozzle and the second nozzle are each replaceable within the impactor with other nozzles having various diameters.

6. An apparatus for measuring contamination particles generated during the manufacture of semiconductor devices according to claim 2, wherein the orifice is replaceable within the impactor with another orifice of different size.

* * * * *